US00PP32265P3

(12) United States Plant Patent
Delbard

(10) Patent No.: US PP32,265 P3
(45) Date of Patent: Oct. 6, 2020

(54) FLORIBUNDA ROSE PLANT NAMED 'DELFLOBLA'

(50) Latin Name: *Rosa hybrida*
Varietal Denomination: DELFLOBLA

(71) Applicant: Societe Nouvelle Pepinieres et Roseraies Georges Delbard SAS, Malicorne (FR)

(72) Inventor: M. Arnaud Delbard, Malicorne (FR)

(73) Assignee: SOCIETE NOUVELLE PEPINIERES ET ROSERAIES GEORGES DELBARD SAS, Malicorne (FR)

( * ) Notice: Subject to any disclaimer, the term of this patent is extended or adjusted under 35 U.S.C. 154(b) by 0 days.

(21) Appl. No.: 16/350,531

(22) Filed: Nov. 30, 2018

(65) Prior Publication Data

US 2020/0178431 P1 Jun. 4, 2020

(51) Int. Cl.
*A01H 5/02* (2018.01)
*A01H 6/74* (2018.01)

(52) U.S. Cl.
USPC ..... Plt./144
CPC ..... *A01H 6/749* (2018.05)

(58) Field of Classification Search
USPC ..... Plt./101, 141, 144
See application file for complete search history.

(56) References Cited

U.S. PATENT DOCUMENTS

2003/0041361 P1 2/2003 Meilland

OTHER PUBLICATIONS

UPOV-PLUTO: Plant Variety Database, Jul. 31, 2019, citation for 'DELFLOBLA'. 1 page (Year: 2015).*

* cited by examiner

*Primary Examiner* — Susan McCormick Ewoldt
*Assistant Examiner* — Karen M Redden
(74) *Attorney, Agent, or Firm* — Buchanan Ingersoll & Rooney P.C.

(57) ABSTRACT

A new and distinct variety of floribunda rose plant, herein referred to by its cultivar name, 'DELFLOBLA', is provided which forms in abundance attractive, white with some pink edges colored double flowers that are long lasting. The vegetation is semi-vigorous to vigorous and the growth habit is bushy. Dark green, bright foliage is formed. The new variety exhibits high resistance to powdery mildew and medium resistance to blackspot. A strong fragrance is produced with different notes, including top notes of rose, grapefruit, and citrus (agrumes); notes of heart of apricot, litchi; and notes of base of some green notes. The new variety is particularly well suited for providing distinctive ornamentation in the landscape.

13 Drawing Sheets

Figure 1:
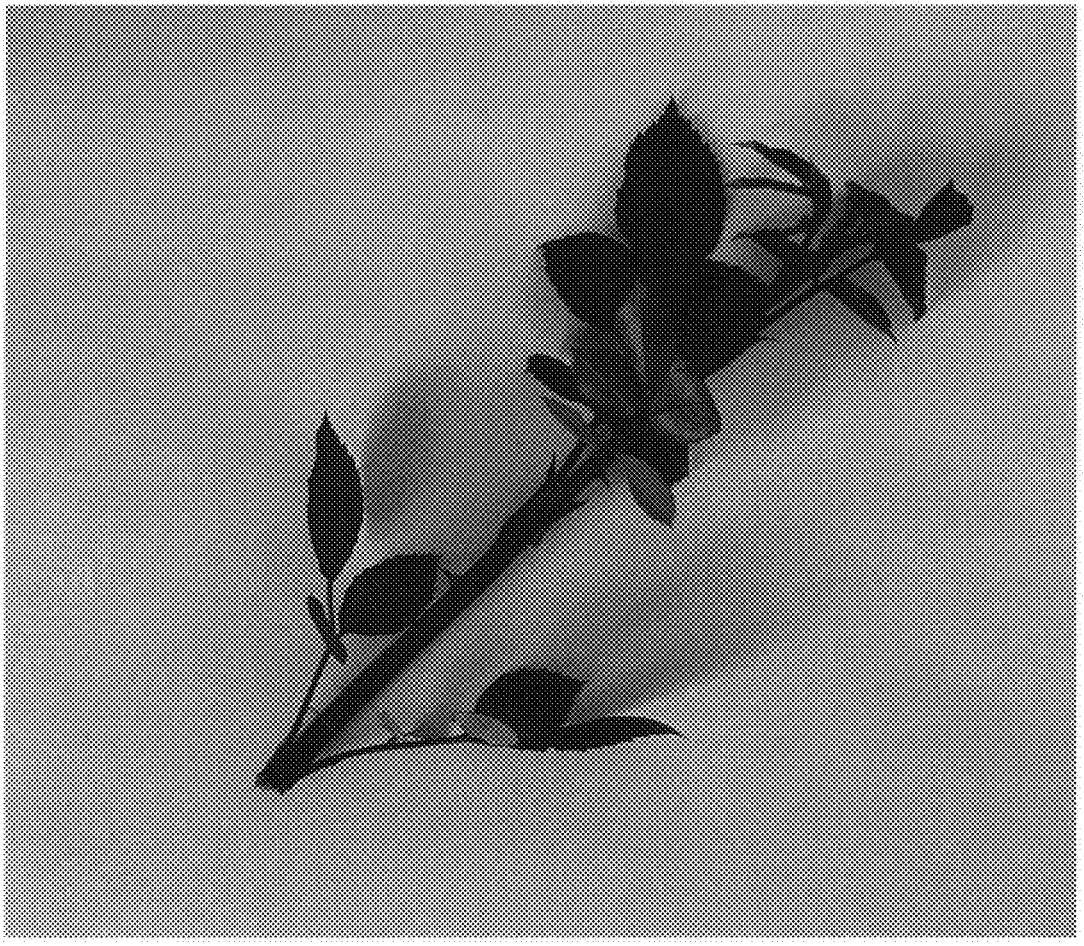

Botanical/commercial classification:
Latin name—*Rosa hybrida.*
Varietal denomination: 'DELFLOBLA'.

SUMMARY OF THE INVENTION

The new variety of *Rosa hybrida* Floribunda Rose Plant of the present invention was created during 2009 at Malicorne, France by artificial pollination wherein two parents were crossed which previously had been studied in the hope that they would contribute the desired characteristics. The female parent (i.e., seed parent) of the new variety was the 'MEICHIBON' variety (U.S. Patent App. Publ. No. 2003-0041361, now abandoned). The male parent (i.e., pollen parent) of the new variety was the 'DELGRAMAU' variety (U.S. Plant Pat. No. 21,510; European Union PBR 29433).

The parentage can be summarized as follows:

'MEICHIBON' x 'DELGRAMAUE'.

The seeds resulting from the above pollination were sown and small plants were obtained which were physically and biologically different from each other. Selective study in 2010 resulted in the identification of a single plant of the new variety.

It was found that the new Floribunda Rose Plant of the present invention possesses the following combination of characteristics:

(a) abundantly forms attractive, white with some pink edges colored double flowers with a strong fragrance,
(b) exhibits a bushy growth habit,
(c) forms semi-vigorous to vigorous vegetation,
(d) provides green mature wood, and
(e) forms attractive ornamental foliage with very good resistance to powdery mildew and medium resistance to blackspot.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the 'MEICHIBON' (i.e., seed parent) exhibits a lower petal count and a larger plant height and width compared to the new variety, whereas the new variety has a stronger fragrance with a characteristic grapefruit note which is lacking in the fragrance of the 'MEICHIBON' variety. Additionally, the 'DELGRAMAUE' variety (i.e., pollen parent) exhibits a lilac colored flower and is more vigorous and more resistant to black spot compared to the new variety, whereas the new variety exhibits white with some pink edges colored flowers. Moreover, the new variety can be readily distinguished from other similar non-parental varieties. For example, the 'Delgrarose' variety (U.S. Plant Pat. No. 21,530) displays pink colored flowers, whereas the new variety displays white colored flowers with some pink edges.

The new variety has been found to undergo asexual propagation in Malicorne, France by a number of routes such as budding (e.g., eye grafting) and cutting. Asexual propagation techniques in Malicorne, France have shown that the characteristics of the new variety are homogeneous, stable, and strictly transmissible by such asexual propagation from one generation to another. Accordingly, the new variety undergoes asexual propagation in a true-to-type manner.

The new variety has been named 'DELFLOBLA'.

BRIEF DESCRIPTION OF THE PHOTOGRAPHS

The accompanying photographs show, as nearly true as it is reasonably possible to make the same in color illustrations of this character, typical specimens of the new variety. The illustrated rose plants of the new variety were grown outside in Malicorne, France.

FIG. 1—illustrates a specimen of a young shoot.

Figure 2:
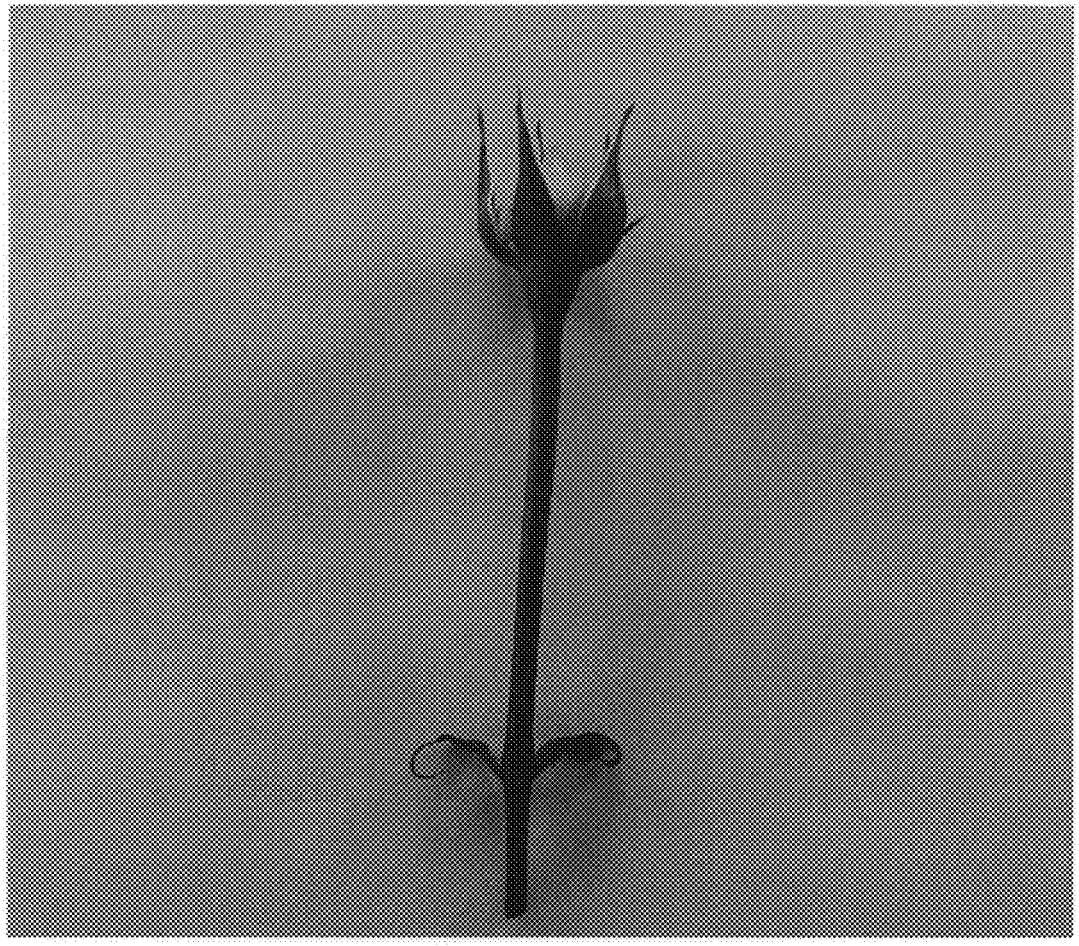

FIG. 2—illustrates a specimen of a floral bud at the opening of the sepals.

Figure 3:
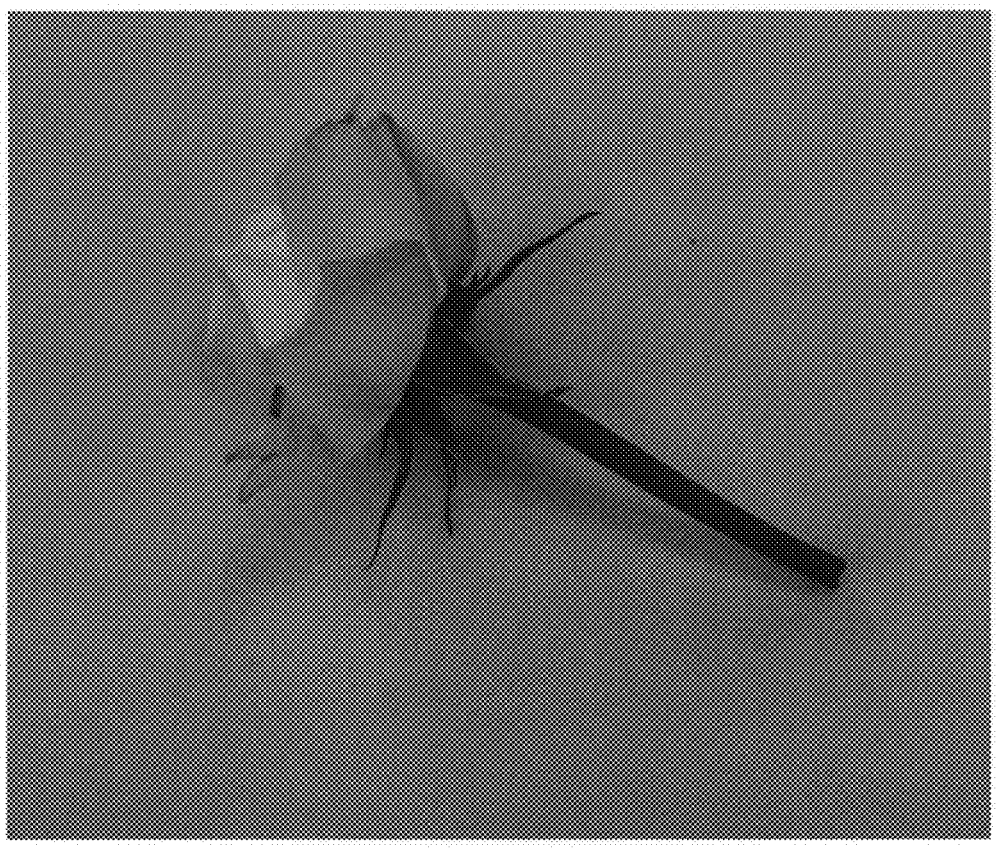

FIG. 3—illustrates a specimen of a floral bud at the opening of the petals.

Figure 4:
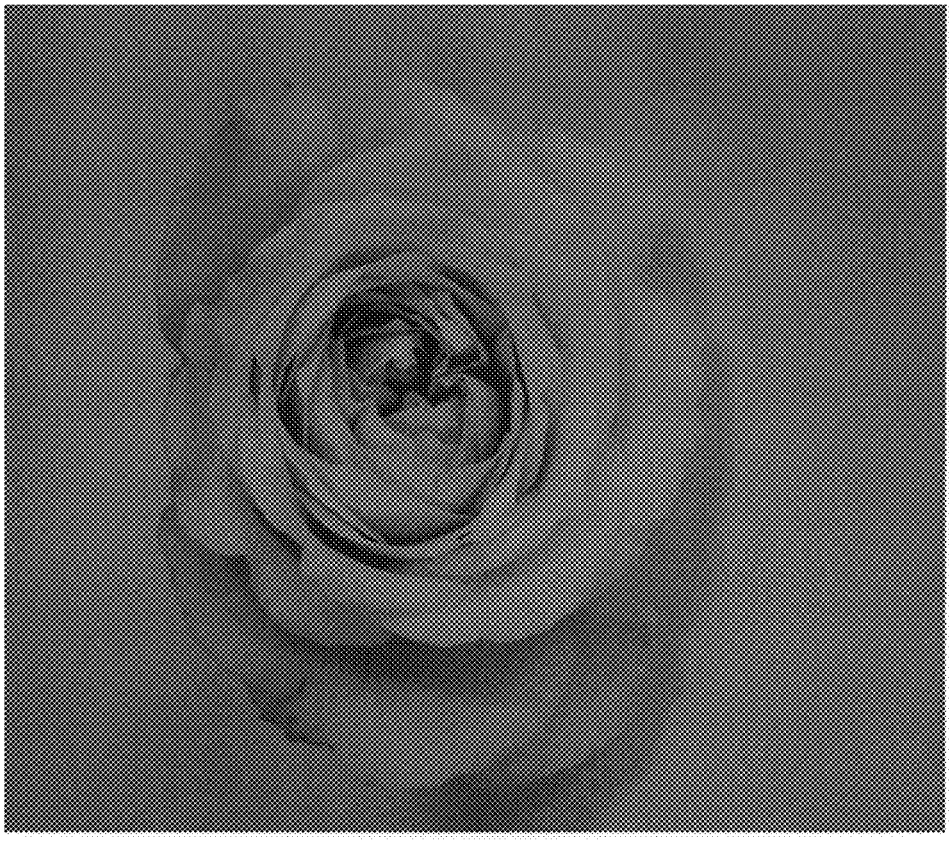

FIG. 4—illustrates a specimen of a flower in the course of opening.

Figure 5:
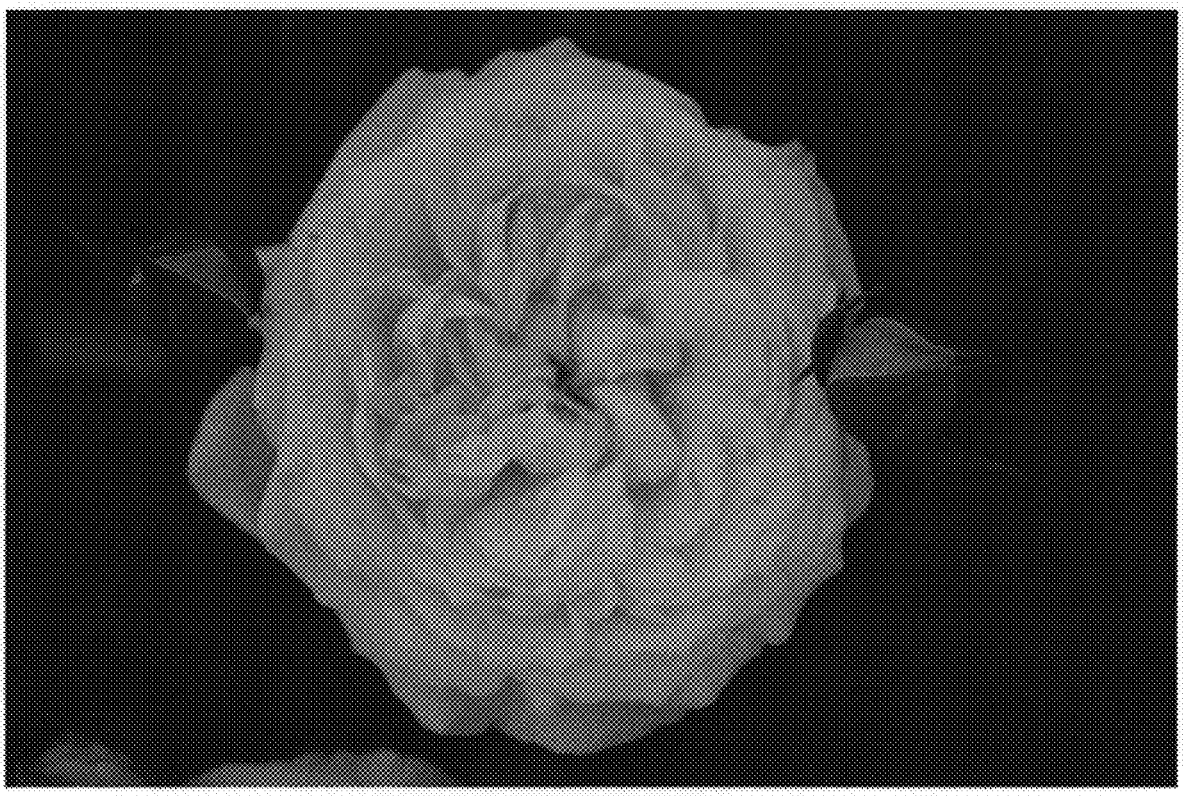

FIG. 5—illustrates a specimen of an open flower—plan view obverse.

Figure 6:
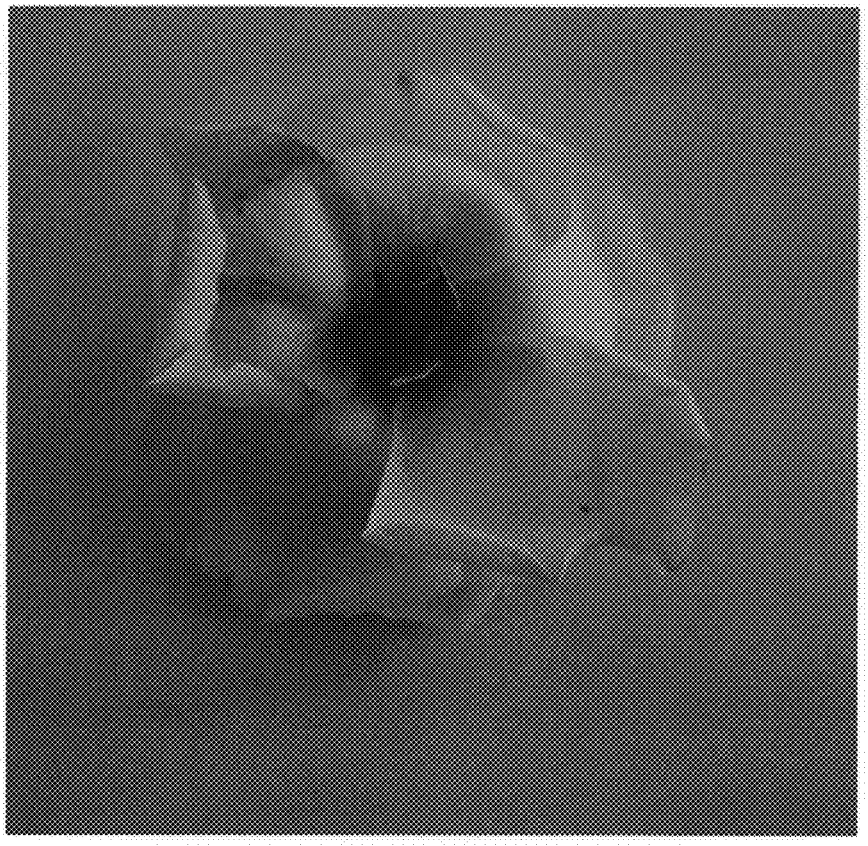

FIG. 6—illustrates a specimen of an open flower—plan view reverse.

Figure 7:
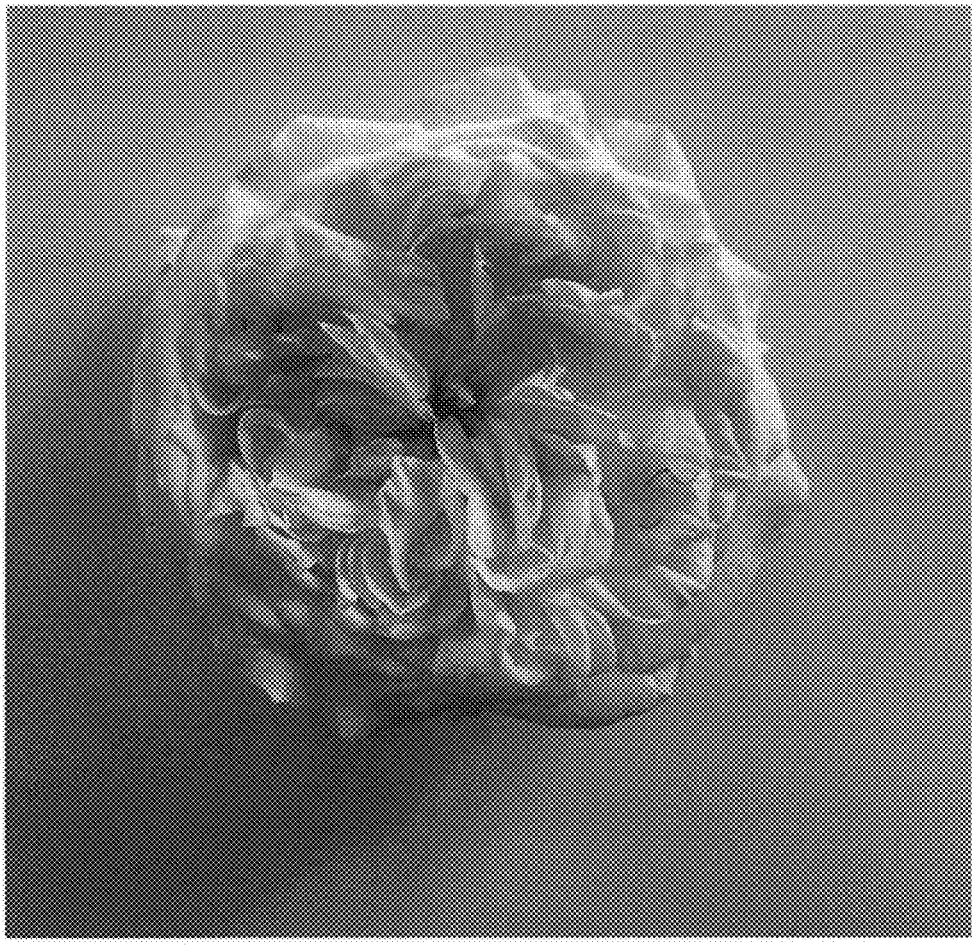

FIG. 7—illustrates a specimen of a fully open flower—plan view obverse.

Figure 8:
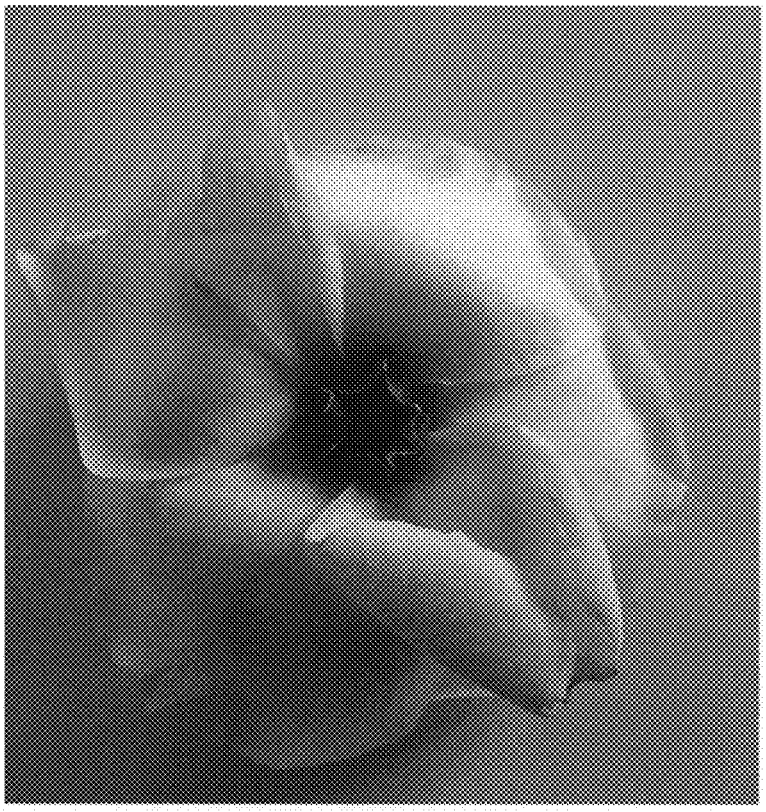

FIG. 8—illustrates a specimen of a fully open flower—plan view reverse.

Figure 9:
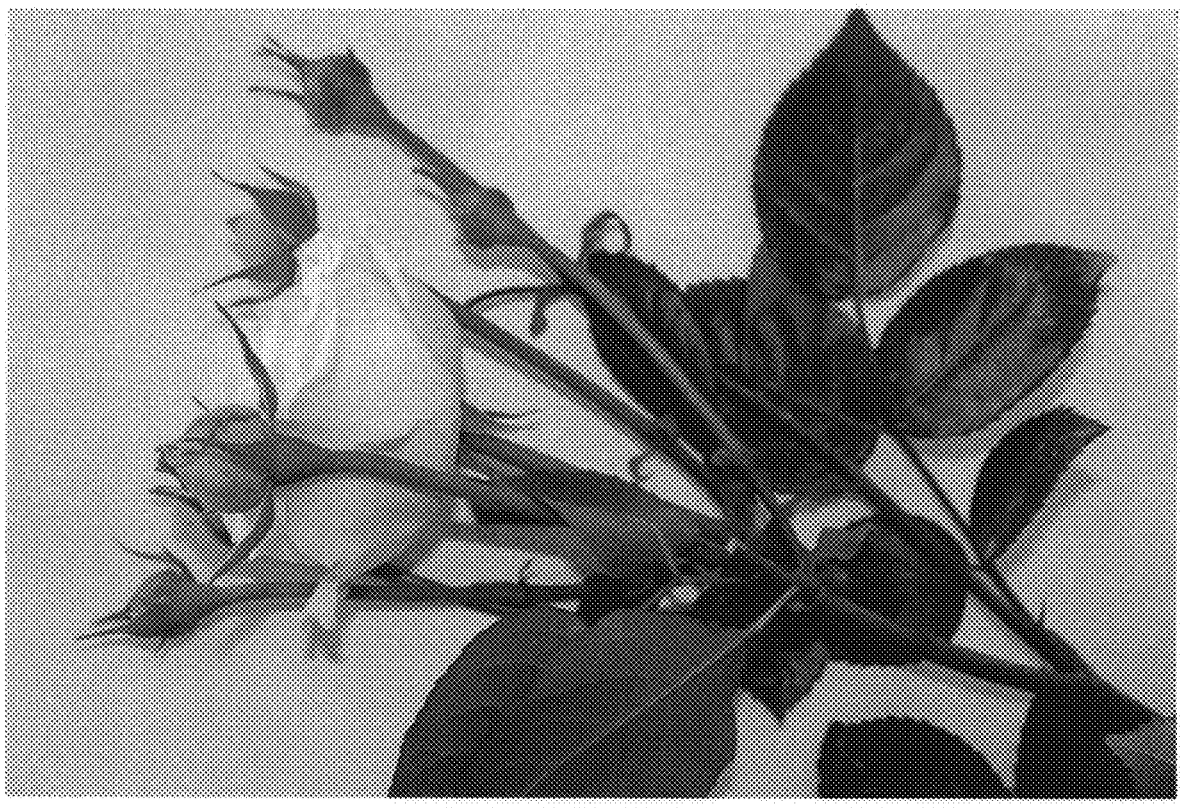

FIG. 9—illustrates a specimen of a flowering stem.

Figure 10:
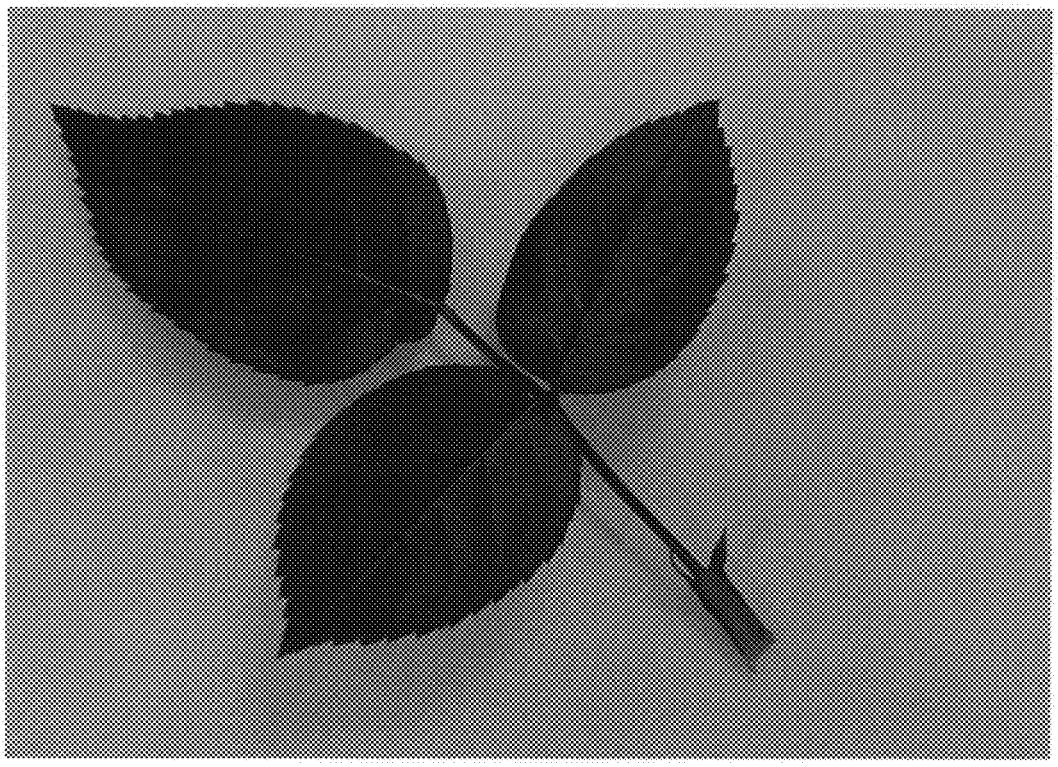

FIG. 10—illustrates a specimen of a leaf with three leaflets—plan view upper surface.

Figure 11:
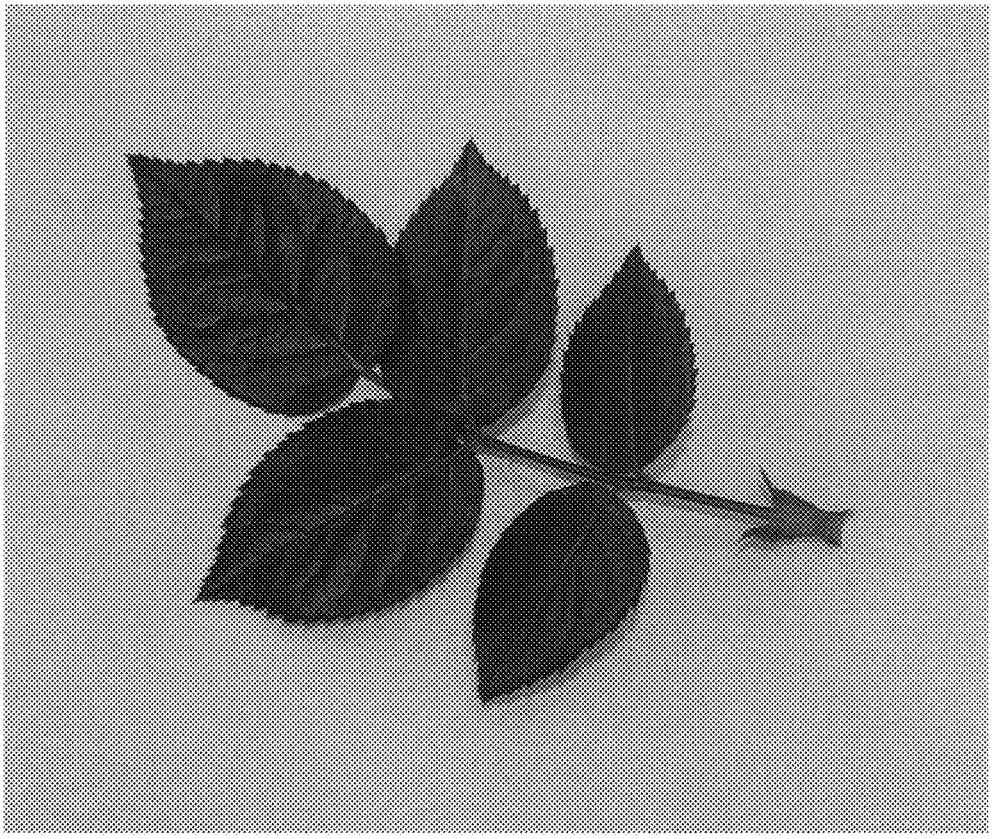

FIG. 11—illustrates a specimen of a leaf with five leaflets—plan view upper surface.

Figure 12:
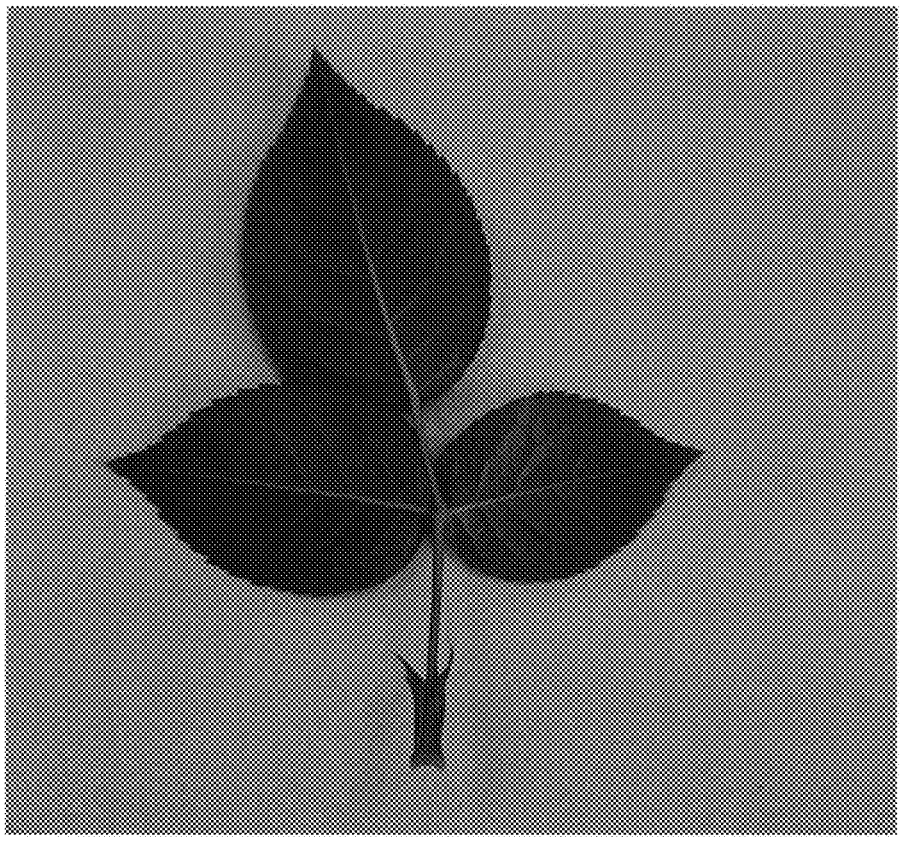

FIG. 12—illustrates a specimen of a leaf with three leaflets—plan view under surface.

Figure 13:
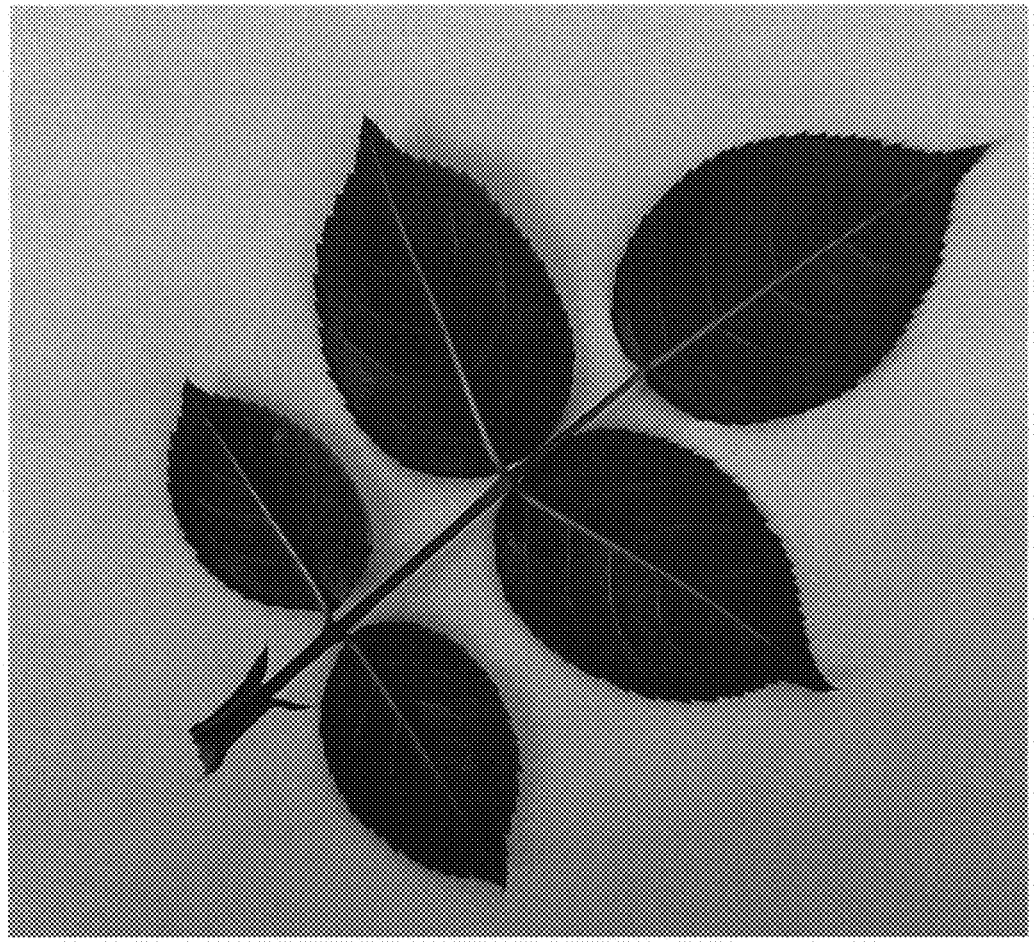

FIG. 13—illustrates a specimen of a leaf with five leaflets—plan view under surface.

DETAILED BOTANICAL DESCRIPTION

The chart used in the identification of colors is that of The Royal Horticultural Society (R.H.S. Colour Chart, 2001 edition). The terminology which precedes reference to the chart has been added to indicate the corresponding color in more common terms. The description is based on the observation of specimens of the new variety, observed outside in Malicorne, France while grafted on *Rosa multiflora* or *Rosa laxa*.

Class: Floribunda Rose Plant.

Plant:

*Habit*.—Bushy.

*Height*.—Commonly 70 to 80 cm, approximately 75 cm on average.

*Width*.—Commonly approximately 40 to 50 cm.

Branches:

*Color*.—Young shoots (approximately 20.0 cm long): commonly combination of near Green Group 137A and Red-Purple Group 59A. — floral stems: commonly near Green Group 137B to Yellow-Green Group 146B. — mature wood: commonly near Green Group 137B.

*Diameter*.—Commonly 8 to 10 mm, approximately 8.5 mm on average.

*Thorns*.—Length: commonly 8 to 9 mm and some thorns irregularly arranged are commonly 2 to 4 mm. — young shoots (approximately 30 cm long): thorns are commonly absent. — color: on floral stems commonly near Grey-Purple Group 183C and on mature wood commonly near Greyed-Purple Group 183C. — configuration: convex on the upper edge and concave on the under edge.

Foliage:

*Number of leaves*.—Commonly approximately 90 to 100.

*General appearance*.—Dark green, bright, consistent with strong glossiness.

*Young shoot*.—Upper surface color: commonly near Green Group 137A and 137B with some bronze coloration. — under surface color: commonly near Greyed-Purple Group 183B with some green coloration on the middle.

*Floral stem*.—Upper surface color: commonly near Green Group 139A. — under surface color: commonly near Green Group 137D and 137C.

*Mature wood*.—Upper surface color: commonly near Green Group 139A. — under surface color: commonly near Green Group 137D and 137C.

*Petiole*.—Prickles: commonly present, often 1 to 2 prickles per petiole. — color: commonly near Greyed-Purple 183B and Greyed-Purple 184B on young shoot; and commonly near Green Group 141B on the upper and under surface of petioles on floral stems and on mature wood. — diameter: approximately 2 mm on average. — length at terminal leaflet: commonly 21 to 25 mm, approximately 22 mm on average, with a standard deviation of 0.22 mm.

*Rachis*.—Length: approximately 5.5 cm on average. — diameter: commonly 1 mm to 2 mm. — texture: smooth. — color: commonly near Yellow-Green Group 144A.

*Stipules*.—Length: commonly 40 to 50 mm, approximately 45 mm on average. — width: commonly 3 to 4 mm, approximately 3.5 mm on average at the midpoint; and commonly 5 to 6 mm, approximately 5.5 mm on average at the distal end. — shape: adnate.

*Leaf serration*.—Present and regular.

Leaflets:

*Number*.—3 and 5.

*Shape*.—Overall obovate; apex is acuminate; rounded to cordate that the base of the terminal leaflet and convex in cross section.

*Venation*.—Pattern is commonly alternately arranged and color is commonly near Yellow-Green Group 145B at the distal end and Yellow-Green Group 145B at the proximal end.

*Size*.—Terminal leaflet: length is commonly 70 to 80 mm, approximately 75 mm on average with a standard deviation of 6.7 mm; and width is approximately 40 to 48 mm, 43 mm on average, with a standard deviation of 0.41 mm.

*Texture*.—Smooth.

Inflorescence:

*Number of blooms per stem or in a cluster*.—Commonly 4 to 6 flowers per stem, approximately 5 on average.

*Duration of blossom*.—Typically lasts on plant around 6 days; typically lasts when cut and in water around 4 days.

*Peduncle*.—Color: commonly Yellow-Green Group 144A, tinted with near Greyed-Purple Group 183D. — length: commonly 52 to 75 mm, approximately 65 mm on average. — diameter: approximately 7 mm on average. — shape: erect, small curve at the bottom. — texture: smooth.

*Sepals*.—Number commonly 5. — shape: overall elongated; apex is sharply pointed. — upper surface color: commonly near Green Group 139C. — under surface color: commonly near Green Group 139C. — size: length is commonly 26 to 33 mm, approximately 30 mm on average; width is approximately 1.1 cm on average. — configuration: one to two sepals commonly possess no extensions, and three sepals commonly possess extensions of approximately 3 to 5 mm. The extensions are denticulate. — texture: smooth.

*Bud*.—Shape: round in longitudinal section just before the opening of the sepals. — length before calyx breaks: commonly 25 to 30 mm, approximately 27 mm on average (calyx included). — length after calyx breaks: commonly 37 to 47 mm, approximately 42 mm on average. — diameter at widest part: commonly 1.7 to 2 cm at stage bud colored; approximately 3.5 cm on average before opening. — color as calyx breaks: commonly near Green Group 140D tinted with Red-Purple Group 60B. — color after calyx breaks (inside): commonly near White Group 155A, Green Group 140D and Red-Purple Group 60D.

*Flower*.—Form: flattened to flattened convex at the upper part when viewed from the side, and flattened to concave at the lower part when viewed from the side. — type: double. — shape: irregularly rounded when viewed from above. — diameter: commonly 8 to 10 cm, approximately 9 cm on average, with a standard deviation of 0.5 cm.

*Fragrance*.—Strong with different notes; notes of top are rose, grapefruit, citrus (agrumes); notes of heart are apricot, litchi; and notes of base are some green notes.

*Petal*.—Number: commonly 100 to 120, approximately 110 on average. — color (middle zone): commonly near White Group 155A on the inner surface. — color (marginal zone): commonly near Red Group 62C on the inner zone edges of the petals and commonly near White Group 155A on the outer surface. — color of the petal spot: commonly near Yellow Group 3C on the inner side and commonly near Green-Yellow Group 3C on the outer side. — drop: partially and in some cases, such as humid conditions, can rotten. — size (second row from outside): length is commonly 49 to 52 mm, with a mean of approximately 50 mm and a standard deviation of 0.4 mm; and width is commonly 48 to 61 mm with a mean of approximately 52 mm and standard deviation of 6 mm. — shape: the first row of petals commonly exhibits a rounded configuration, the base of the petals is slightly more ovate; overall petal shape is irregularly rounded; shape of petal apex is flat; shape of petal base is flattened convex. — texture: smooth and soft — margin: undulation is medium and reflexing of the margins is medium.

*Stamen*.—Number: approximately 2 to 7. — arrangement: irregular. — anthers: color is commonly near Yellow Group 3C when immature; and all open at approximately the same time. — filaments: length is approximately 1 to 3 mm on average when the flower is fully open and color is commonly near Yellow Group 3C.

*Pistils*.—Number: approximately 18 to 30 on average. — style: color is commonly near Yellow-Green Group 145D; and length is approximately 8 to 12 mm. — stigma: color is commonly near Yellow-Green Group 150C; position is generally superior to the anthers.

*Pollen*.—Sparse in quantity and color is commonly near Yellow-Green Group 145D.

*Hips/seed*.—None observed to date.

Development:

*Vegetation*.—Semi-vigorous to vigorous.

*Blooming*.—Abundant and almost continuous.

*Aptitude to forcing*.—Excellent.

*USDA hardiness zone*.—Not observed.

*Resistance to disease*.—Medium resistance to blackspot (*Diplocarpon rosae*); and very good resistance to powdery mildew (*Podosphaera pannosa*).

Plants of the 'DELFLOBLA' variety have not been observed under all possible environmental conditions to date. Accordingly, it is possible that the phenotypic expression may vary somewhat with changes in light intensity and duration, cultural practices, and other environmental conditions.

I claim:

1. A new and distinct Floribunda Rose plant characterized by the following combination of characteristics:

(a) abundantly forms attractive, white with some pink edges colored double flowers with a strong fragrance,
(b) exhibits a bushy growth habit,
(c) forms semi-vigorous to vigorous vegetation,
(d) provides green mature wood, and
(e) forms attractive ornamental foliage with very good resistance to powdery mildew and medium resistance to blackspot;

substantially as herein shown and described.

* * * * *